United States Patent [19]
Newbold, III et al.

[11] Patent Number: 5,650,551
[45] Date of Patent: Jul. 22, 1997

[54] NEWBOLD'S DIAMOND, A DENSELY FOLIOLATE, COMPLANATE LEATHERLEAF FERN

[75] Inventors: William S. Newbold, III; John R. Newbold, Jr., both of Crescent City, Fla.

[73] Assignee: Jack K. Austin, Umatilla, Fla.

[21] Appl. No.: 423,667

[22] Filed: Apr. 17, 1995

Related U.S. Application Data

[63] Continuation-in-part of Ser. No. 165,709, Dec. 13, 1993, Pat. No. Plant 9,113.

[51] Int. Cl.$^6$ .................................. A01H 5/04; A01H 9/00
[52] U.S. Cl. .............................................................. 800/200
[58] Field of Search ........................ Plt./88.3; 800/200, 800/230, DIG. 52

[56] References Cited

U.S. PATENT DOCUMENTS

P.P. 9,113  4/1995  Newbold et al. ................. Plt./88.3

OTHER PUBLICATIONS

Huxley, A., et al., (Eds.), "Rumohra", The New RHS Dictionary of Gardening 4, Apr. 1992, The Stockton Press, N.Y., pp. 147, 148.

Primary Examiner—James R. Feyrer
Attorney, Agent, or Firm—Allen, Dyer, Doppelt, Milbrath & Gilchrist, P.A.

[57] ABSTRACT

A new variety of leatherleaf fern having a diamondlike shape, arose as a vegetative mutation from a plant of *Rumohra adiantiformis* (Forst.f.) Ching that was under normal cultivation conditions. Through successful propagations by both rhizome division and meristem tissue culture, it has been ascertained that the specimens of the new variety may be distinguished from those of the parent by the fronds, which are more densely foliolate, more complanate, more symmetrical in the foliate portion of the frond, with pinnae tending to be subopposite, of a darker color, larger size, and with a fuller distal acumination. The new variety has advantages for cut flower arrangements because the complanate pinnae present a pleasing and full appearance, thus improving the aesthetic and market value of the arrangements. The superior lasting qualities and resistance to fading of the deep green color further enhances the utility of the foliage over a spectrum of end products.

16 Claims, 5 Drawing Sheets
(4 of 5 Drawing(s) in Color)

NEWBOLD'S DIAMOND, A DENSELY FOLIOLATE, COMPLANATE LEATHERLEAF FERN

CROSS REFERENCE TO RELATED APPLICATION

This application is a continuation-in-part of our application Ser. No. 08/165,709, filed Dec. 13, 1993, now U.S. Patent Number Plant 9,113.

BACKGROUND OF THE INVENTION

1. Field of the Invention

The present invention relates to decorative foliage, and, more particularly, to new and distinct varieties of fern, specifically, to a new and distinct variety of leatherleaf fern.

2. Description of Related Art

Ferns belong to the phylum Pterophyta. In the wild, the life cycle of ferns proceeds via alternating haploid and diploid generations. The asexual, diploid, sporophyte generation represents the fern plant as it is commonly known. The mature fern is comprised of a fleshy stem, or rhizome, adventitious roots and frondiform leaves. On the underside of the fertile leaves small brown areas representing sori may be produced. The sorus is comprized of groups of spore cases, or sporangia. When a spore germinates, it develops into a haploid, ephemeral sexual fern gametophyte called the prothallium, which is a small, flat, green structure having an apical notch and with a number of rhizoids growing on its underside. Also on the underside of the multistratose portion of the prothallium are the female sexual organs each being an egg containing archegonium. The male sex organ, or antheridium is commonly borne on the lower surface or near the margin of the unistratose wing. Sperm are biflagellated and motile and are released before archegonia are receptive thus creating the possibility in nature for cross-fertilization with prothallia having receptive archegonia. Unisexual prothallia are uncommon among the true ferns and self-fertilization is reported to be a common means to produce the perennial frond-bearing sporophyte. The rhizome is commonly parallel to the substrate and may be on the surface or somewhat below it. The roots originate as adventitious outgrowths from the rhizome which serve to anchor the plant and function in absorption of water and minerals.

The leatherleaf fern, *Rumohra adiantiformis* (Forst.f.) Ching (FIG. 1), also known as the leather fern or iron fern, has a varied taxonomic history, having been assigned previously to the genera Polystichum and Polypodium, and placed into the plant families Polypodiaceae, Aspidiaceae, and Davalliaceae. Some recent publications indicate that Rumohra represents a monotypic genus containing the single species *R. adiantiformis*. The genus has been placed in several families, but it is said that most evidence points to possible affinities with at least two families, the Dryopteridaceae and to a lesser extent with Davalliaceae. It is noteworthy in this regard that, although six species are claimed in Huxley's *Dictionary of Gardening* (1992), only the single type species is characterized and other txa mentioned appear to be assigned by indirect reference to other genera.

Accordingly, it is considered that *Rumohra adiantiformis* is a single botanical species with a range of variation sufficient that populations may be recognized at the level of botanical "form." For instance, Huxley refers to *Rumohra adiantiformis* "Cape Form," which is distinct by its fronds, which may reach as much as 1.5 m when grown in terrestrial fern mix, where warm and well drained. Other forms are generally endowed with smaller fronds, commonly not exceeding 90×75 cm when grown under suitable conditions. The usual forms of *Rumohra adiantiformis* under cultivation on slabs as specimen plants have medium-sized fronds that are reported to reach up to 60 cm long.

Variants of *Rumohra adiantiformis* are known to exist, but consistently and wisely employed variant cultivar names are unknown. The variant form, "Newbold's Diamond Leatherleaf Fern," represents a distinctive embodiment within the species selected for a combination of characteristics desirable for the foliage and floriculture industry.

True ferns commonly appear in the marketplace as foliage plants and also in the floral industry in arrangements. *Rumohra adiantiformis* was first produced for floral arrangements in Florida during the 1930s and 1940s, but major plantings were not started until the early 1950s. Since the 1950s the leatherleaf fern has been reported to have been used more frequently and is believed to be the most widely used cut foliage in commercial floral arrangements and corsages. The popularity of cut fronds of the leatherleaf fern derive from its superior keeping quality, ease of shipping, and versatile design qualities resulting from its form, texture, and color, as compared with asparagus fern, for instance. The asparagus fern is so finely divided, bushy, and pale in color, that is does not provide the substantive background for an arrangement as that created by the leatherleaf fern, because the leatherleaf fern leaves (fronds) are sturdy and glossy dark or deep green. Some growers have given names to a few selections of leatherleaf fern, but until now it is not known to have been sold by a cultivar name.

Leatherleaf fern is normally propagated commercially by rhizome divisions or clumps to ensure perpetuation of plants with desirable characteristics. It would be anticipated normally that leatherleaf fern propagated from spores would show variation from the parent as a result of genetic recombinations, and such sexually produced progeny may not be true to type. This relatively slow-growing species may require up to a full year for the sexually produced sporophyte to complete development of a mature rhizome and fully formed fronds of size suitable for market. Therefore, propagation by vegetative means is clearly the recourse of choice for the grower.

In the enormous market for foliage fillers for flower arrangements in the florist industry, a need exists for an attractive, hardy, and readily adaptable foliage. The leatherleaf fern has captured an increasing share of the market because of its well-known keeping and shipping qualities, as well as its rich color and pleasing silhouette as a background in floral arrangements. Although considerable variation exists among fronds of *Rumohra adiantiformis* found in the trade, no obvious attempt has been made to present a superior frond for the trade.

A clearly superior frond would have a predictable size, closely spaced pinnae, a rich green color, and a symmetrical profile for the whole blade and for each of the compound pinnae. It must be nearly complanate and rigid but not brittle, retain color for long periods, be easily packed and unpacked, withstand shipping well, and resist wilting.

Propagation must be efficient, tissue culture successful for production of predictable plants, and growing conditions easily maintained with a minimum of hand labor. Plants must grow year around for a continuous production to meet the need of the market.

A cause of loss to the grower during harvesting and shipping is breakage of pinnae or pinnules, which renders the frond unsalable. The pinnae of the currently sold varieties of leatherleaf fern are typically canted away from the plane formed by the rachis and pinnae. Because fronds are harvested and shipped atop one another, a complanate habit characteristic for a new variety to reduce breakage or damage in shipment would be desirable.

Even though one or more of these features may be found among fronds currently in the trade, none consistently realizes a full suite of optimal characteristics.

SUMMARY OF THE INVENTION

The variety 'Newbold's Diamond' has been deposited with the ATCC under the identification *Rumohra adiantiformis diamonte* F904-CB and has been assigned deposit number ATCC 97571. It is anticipated that the plant 'Newbold's Diamond' may be known synonymously by *R. adiantiformis diamonte* under which it has been deposited.

A general object of the present invention is the development of a variety of *Rumohra adiantiformis* species that is distinguishable from others and through propagation is productive of specimens with fronds of a symmetrical shape and a complanate aspect.

It is also an object of the present invention to provide a new variety of leatherleaf fern that has flatter fronds that present an appearance of denser foliage and also are less susceptible to breakage during harvesting and shipping.

It is a further object to provide a new variety of leatherleaf fern having more nearly opposite proximal pinnae, which lend a denser and more symmetric appearance to the frond.

It is an additional object to provide a new variety of leatherleaf fern having a darker and/or deeper green color, thus presenting a richer appearance.

It is another object to provide a new variety of leatherleaf fern that has superior lasting qualities.

The above and other objects of the invention have been realized by the development of the new fern plant variety described hereinafter. The variety of leatherleaf fern plant of the present invention is distinct from the usual leatherleaf fern plant produced under cultivation. The new variety bears fronds having the characteristic of relatively complanate pinnae, in contradistinction to typically found fronds, whose pinnae are obliquely inserted relative to the plane of the rachis and rachillae. The flatter fronds of the new variety accordingly present a denser appearance, thus dramatically improving the market value of the fronds, because each frond appears richer, and fewer fronds may be required to achieve the same effect in a floral arrangement.

In addition to the higher value of full fronds in large arrangements, the symmetry and composition of the frond makes it amenable to being divided for use in smaller arrangements and corsages. Because fronds are harvested and shipped one atop another, this feature of flatness further provides fronds less susceptible to breakage during harvesting and shipping than those of the parent plant. This is because pinnae that lie at an angle to the plane formed by the rachis and the rachillae can be crushed or entangled and easily broken by neighboring fronds during packing or separation following delivery. Therefore, the flatness feature improves the market value of the fronds further by reducing loss incurred during shipping and handling.

Additional elements of the present invention comprise the leatherleaf fern fronds produced by the leatherleaf fern plant in accordance with the preceding description.

An additional characteristic present in a preferred embodiment of the present invention comprises the fronds of the aforementioned leatherleaf fern plant variety having more closely subopposite proximal pinnae than those commonly alternate and distant proximal pinnae of the parent plant. This characteristic permits the fronds thereby to present a denser and more symmetric appearance than those of the parent plant.

A further characteristic of the fronds of the preferred embodiment of the leatherleaf fern plant variety is the color, which is a generally darker and/or deeper green color than in the parent plant fronds. This more intense color also adds to the richer appearance of the new variety over the parent plant fronds. Again, the fronds and plants resulting from spores form elements of the invention.

Another feature of the plant of the present invention is that the fronds of the preferred embodiment have a more distinct distal acumination than those of the parent plant; that is, the distal end has been found to come to a more pronounced point than that of the parent fronds. Again, the fronds also form elements of the invention.

Through successive propagations it has been ascertained that specimens of the new plant are distinguishable from those of its antecedents and related variants known to the inventors by a growth habit that is evident in specimens propagated and grown in Eustis, Fla., as combining the listed principal characteristics.

The features that characterize the invention will be better understood from the following description read in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE INVENTION

A description of the preferred embodiment of the present invention will now be presented with reference to FIGS. 1-5.

Figure 1:
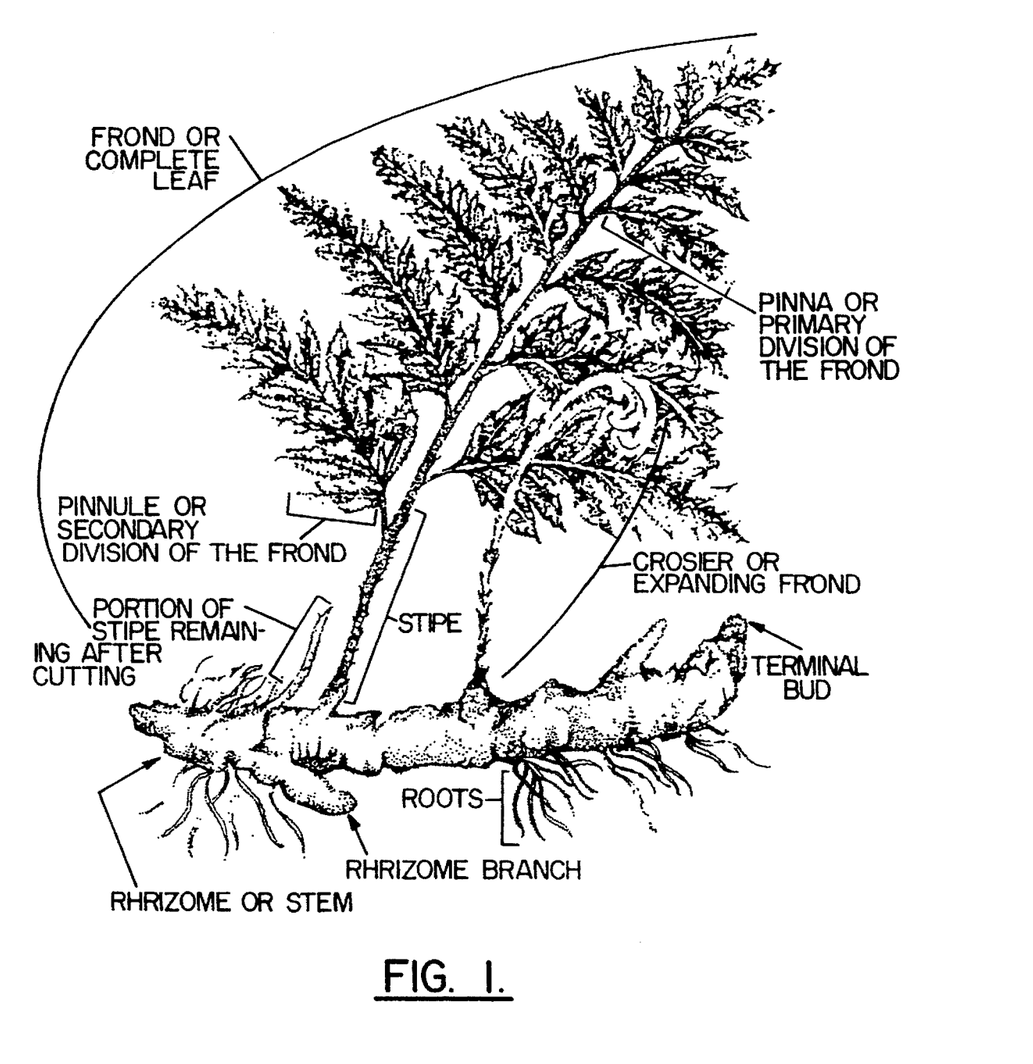
FIG. 1 illustrates the parts of the leatherleaf fern. (Taken from "Commercial Leatherleaf Fern Production in Florida," R. W. Henley, B. Tija, and L. L. Loadholtz, Florida Cooperative Extension Service, Gainesville, Fla.)
Figure 2:
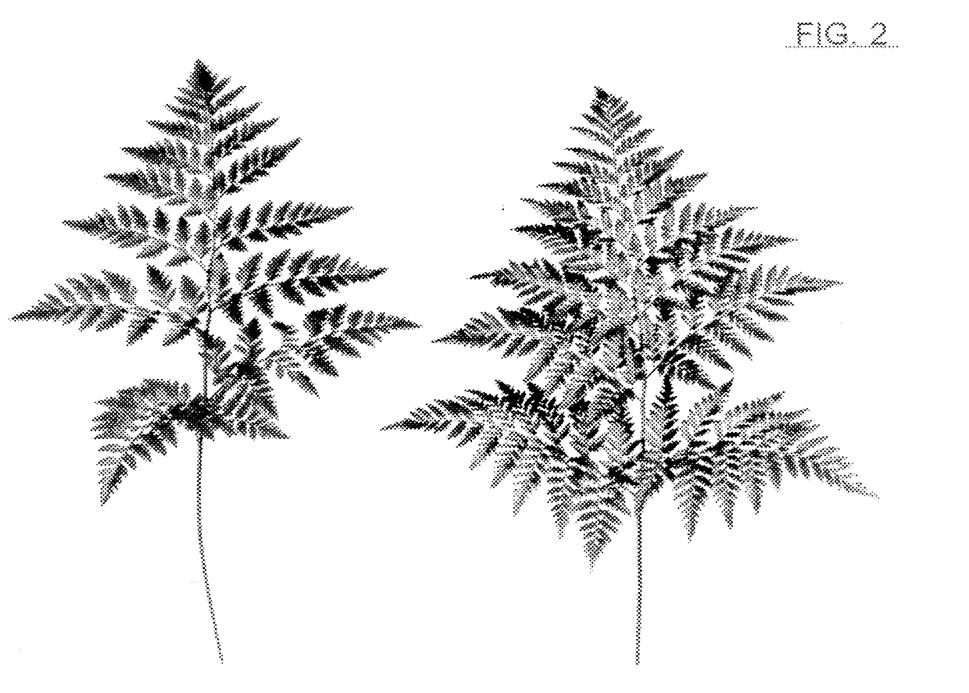
FIG. 2 depicts the previously known *Rumohra adiantiformis* beside a typical specimen of the new variety of *Rumohra adiantiformis*.

Field run *Rumohra adiantiformis* fronds closely approximate the appearance rendered in the drawings in FIG. 1. A photograph in Mickel's *Ferns for American Gardens* is also representative of the usual form of the frond. In neither of these depictions is the canted angle of the pinnae relative to the plane of the primary rachis and the whole frond indicated in a substantive manner. Further, in descriptions of which the inventors are aware, no mention is made of this attribute of the leatherleaf fern, which is significant for the floriculture industry, as mentioned above. An examination of fresh fronds representing field samples collected from different growers has confirmed the characteristics of the species presented by Huxley et al. in *The New Royal Horticultural Society Dictionary of Gardening* (1992).

The new variety of leatherleaf fern (*Rumohra adiantiformis*) of the present invention, named "Newbold's Diamond Leatherleaf Fern" by the inventors for its diamondlike shape, arose as a vegetative mutation from a plant of *Rumohra adiantiformis* that was grown under normal cultivation conditions in a nursery in Crescent City, Fla. Since the initial discovery of the new variety, the plant has been asexually reproduced by the inventors by the propagation of rhizome divisions taken from the original plant specimen.

Satisfactory growing conditions for the plant of the present invention are comparable to those of the parent, so that no change in horticultural regimes is required.

Although sori form on some fronds, no evidence has been found for gametophyte development or subsequent sexual reproduction in the field.

In addition to rhizome division, the inventors have successfully propagated the new variety with the use of meristem tissue culture. Through successful propagations by both methods, it has been ascertained that the specimens of the new variety may be distinguished from those of the parent, and from other clones known to the inventor, by the fronds, which are more densely foliolate, more complanate, more symmetrical in the foliate portion of the frond, with proximal pinnae tending to be subopposite, of a darker and/or deeper color, larger size, and with a more distinct distal acumination (compare the specimens shown in FIG. 2).

The new variety has advantages for cut flower arrangements because the complanate pinnae present a pleasing and full appearance, thus improving the aesthetic and market value of the arrangements. The superior lasting qualities and resistance to fading of the rich green color further enhances the utility of the foliage over a spectrum of end products ranging from the use of a single basal pinna for corsages to elaborate floral displays on a large scale. Because these characteristics are sought by florists, the variety of the preferred embodiment of the invention is expected to meet the need for an improved leatherleaf fern frond.

Figure 3:
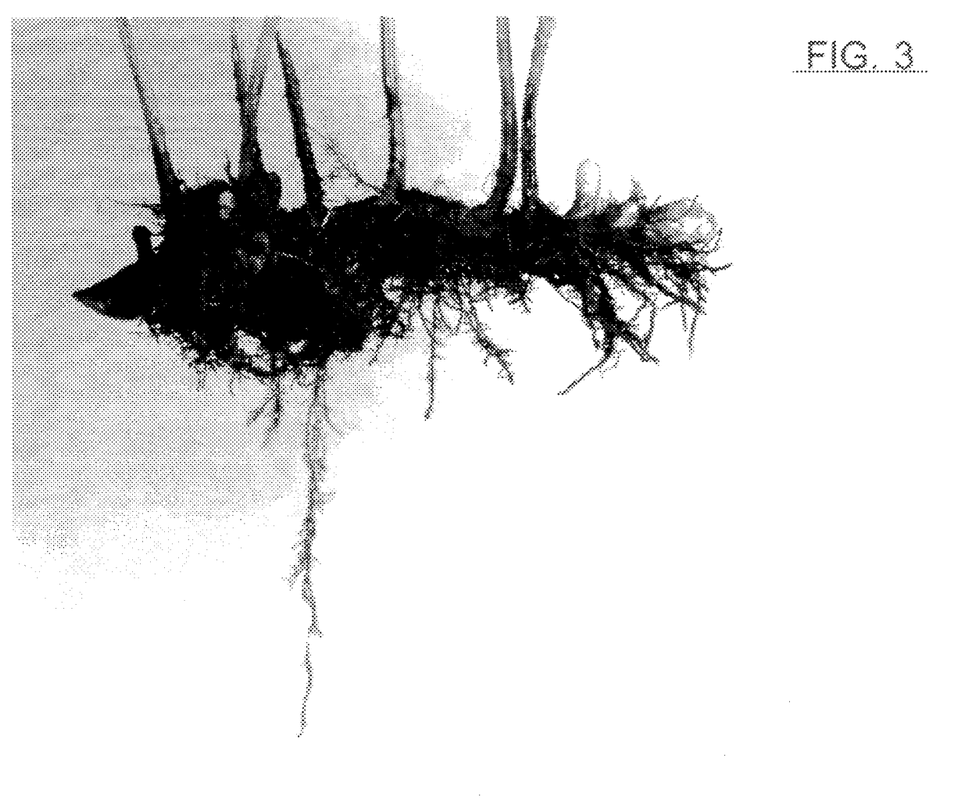
FIG. 3 shows a portion of an underground rhizome and roots, to which are attached fronds. The stipes are shown having scales.
Figure 4:
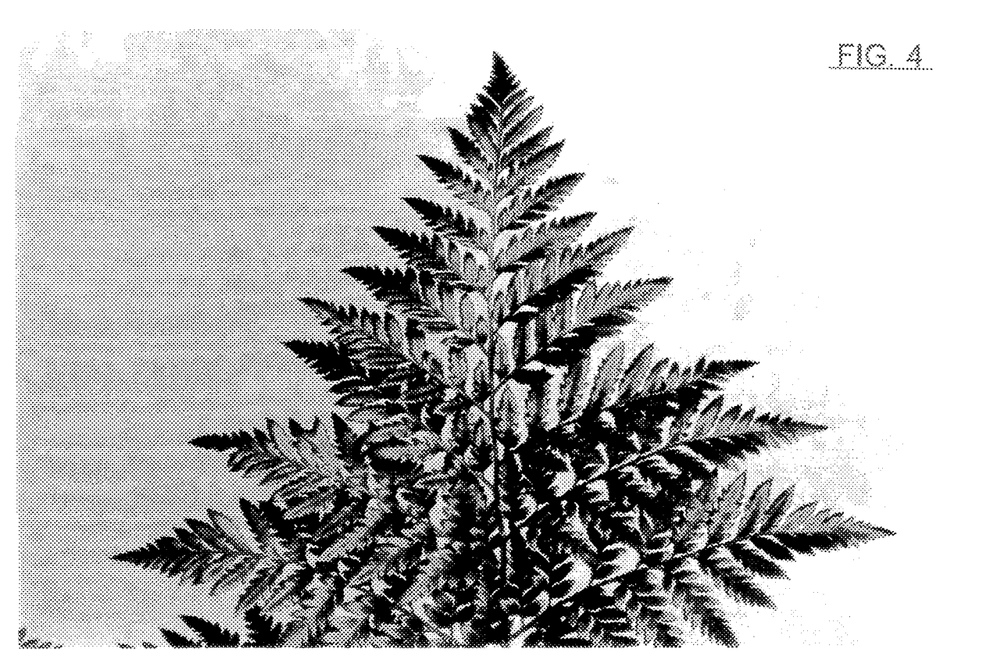
FIG. 4 shows the adaxial surface of a frond.
Figure 5:
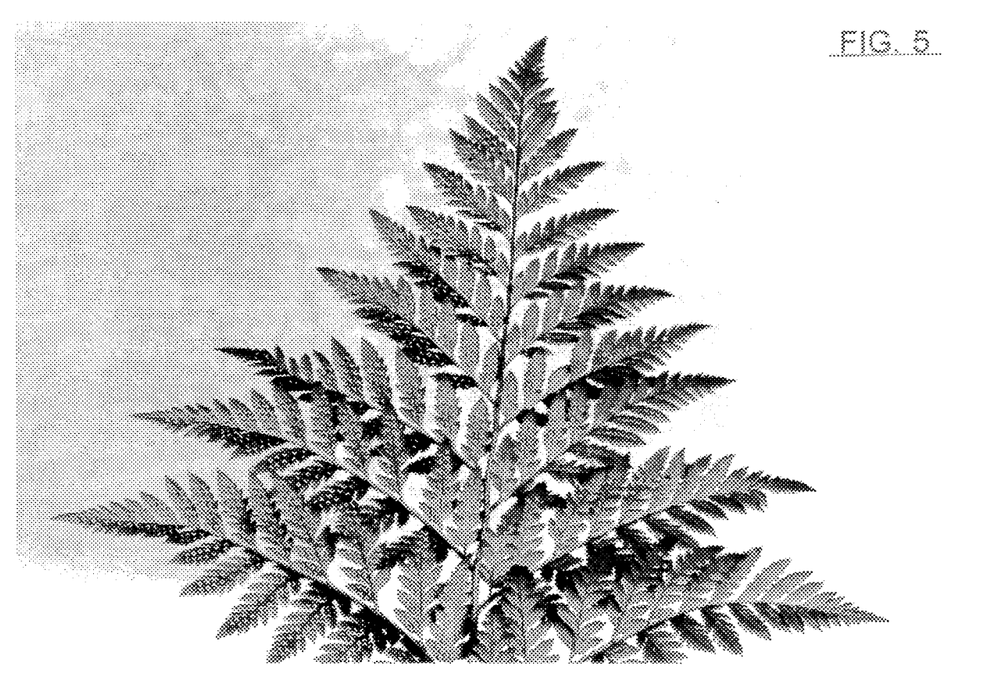
FIG. 5 shows the abaxial surface of a frond having pinnae with sori.

FIGS. 3–5 illustrate the features of the leatherleaf fern variety of the present invention that will be detailed in the following discussion. FIG. 3 shows a portion of an underground rhizome and roots, to which are attached fronds. The stipes are shown having scales. FIG. 4 shows the adaxial surface of a frond, and FIG. 5 shows the abaxial surface of a frond having pinnae with sori.

The source for the description of colors and hues used in the following is the ISCC-NBS Method of Designating Colors (U.S. Dept. of Commerce, National Bureau of Standards, Special Publication 440, issued December, 1975), the named colors having been interpreted from color notations derived by comparison with color specimens in the Munsell Book of Color and the Munsell Limit Color Cascade (Macbeth, A Division of Kollmorgen Corp., 2441 North Calvert St., Baltimore, Md. 21218, March, 1979).

The botanic classification of the variety of the present invention is Family Dryopteridaceae (fern family), Genus Rumohra, species *adiantiformis*. The form is terrestrial, herbaceous, shade-loving, rhizomatous, with separate coriaceous-appearing fronds arising behind the terminal bud becoming erect to inclined when mature.

The detailed description to follow is based upon observations made during the months of August and September of well-fertilized fully mature plants that were grown during nursery conditions under a 73% cloth shade cover in the Umatilla, Fla., area, wherein temperatures range from about 75° to 98° F. during the summer months and from about 30° to 80° F. during the winter months. The differences between fronds of the "typical" and the leatherleaf fern of the present invention are not dependent upon lighting conditions; i.e., shading is not critical to the specifics of the frond pattern produced.

The stems are rhizomatous with an adventitious root system. The rhizomes are elongate, irregularly branched, and prostrate at or below ground level with adventitious, black, fibrous roots. The texture of the underground rhizomes is succulent near the apex with small, distant, deltoid, membranous scales that are usually between 1 and 2 mm wide and 1 and 3 mm long, with the rhizome becoming woody with age with scales eroded or lacking and presenting a scruffy appearance where old leaf bases have persisted. The shape of the rhizomes is generally terete with tendencies to become torose or nodiform; the diameter is usually between 7 and 17 mm. (These are apparently the same as or very close in the parent.)

The color of the rhizomes is commonly strong yellow green (2.5GY6/8)(2.5GY7/8)(2.5GY7/10), brilliant yellow green (2.5GY8/10) in the distal portions, becoming brilliant greenish yellow (near 7.5Y8/8) (near 7.5Y8/10) (near 10Y8/10), strong greenish yellow (near 7.5Y8/8) (near 7.5Y8/10) (near 10Y8/10), moderate greenish yellow (near 7.5Y8/8), light greenish yellow (near 7.5Y8/8) with age and darkening to brownish orange (5R5/8) and/or strong yellowish brown (7.5R5/8) and with the intact scales in distal areas being moderate reddish brown (10R3/4) (7.5R3/4) (7.5R3/6).

The roots are adventitious, fibrous, woody, usually subterranean in cultivation, freely branched, and black in appearance. Their diameter is usually between 0.5 and 1.5 mm, and their length, usually between 10 and 40 cm. Their color is commonly black, dark grayish brown (near 5YR2.5/1), brownish gray (near 5YR2.5/1), and/or grayish brown (near 5YR2.5/1).

The fronds are robust, long stipitate, with a bipinnate to tripinnate frond having compound pinnae below and foliolate pinnae above, the pinnae being subopposite proximally on the rachis and alternate distally with initial growth showing circinnate vernation. The fronds arise singly from the rhizome with a shape widely trullate in outline excluding incisions between pinnae and pinnules.

The length of the fronds, including stipe, is usually between 50 and 70 cm at maturity; excluding the stipe, the length is usually between 30 and 47 cm at maturity. The maximum width is usually between 25 and 45 cm at maturity.

The stipe is herbaceous and fleshy during initial emergence, becoming brittle and hardening with age. The mature stipe has a woolly appearance because of numerous narrowly triangular to subulate irregularly wavy, often evanescent, scales usually between 1 and 2 mm wide and between 4 and 8 mm long which are commonly moderate reddish brown (10R4/6), strong brown (2.5YR4/8) (5YR4/6) (7.5YR4/6), grayish reddish orange (2.5YR5/6), brownish orange (2.5YR5/8) (near 2.5YR5/6), and/or light brown (near 2.5YR5/6). The shape is generally oblong-elliptic in cross-section with an adaxial, rounded, shallow groove. The length is usually between 22 and 30 cm at maturity when measured between attachment to the rhizome and the origin of the basal pinna and the thickness is usually between 3 and 5 mm measured adaxially/abaxiallY and between 4 and 6 mm measured laterally intermediate between the rhizome attachment and the origin of the basal pinna.

Generally, the color in the basal area is dominated by reddish brown hues and both the abaxial side color and the adaxial side color in the distal stipe area is dominated by olive, olive green and/or yellow green hues. Specifically, the basal area color is commonly moderate reddish brown (7.5R3/4), dark grayish reddish brown (near 10R2.5/2) (near 10R2.5/1) (near 2.5YR2.5/2), dark reddish gray (near 10R2.5/1), and/or grayish reddish brown (near 10R2.5/2) (near 10R3/2) (near 2.5YR2.5/2) (2.5YR3/2) and in the distal area the color is commonly light olive (10Y5/6), moderate yellow green (2.5GY5/6) (2.5GY5/4) (5GY5/4) (5GY5/6) (7.5GY5/4), moderate olive green (2.5GY4/4) (5GY4/4) (7.5GY4/4), and/or moderate olive (10Y4/6).

The rachis is herbaceous and fleshly when maturing and rapidly hardening with age, and is endowed at maturity with scattered small narrowly triangular to subulate, often evanescent scales that are commonly moderate reddish brown (10R4/6), strong brown (2.5YR4/8) (5YR4/6) (7.5YR4/6) grayish reddish orange (2.5YR5/6), brownish orange (2.5YR5/8) (near 2.5YR5/6), and/or light brown (near 2.5YR5/6). The stipe shape is generally ovoid-elliptic in cross section with an adaxial rounded, shallow groove.

The length of the rachis is usually between 27 and 47 cm at maturity when measured from the origin of the basal pinna to the base of the distal lamina. The rachis thickness is usually between 2 and 3 mm in diameter when measured adaxial/abaxially, and between 2 and 4 mm when measured laterally between the fifth and sixth pinna counting from the lowermost pinna.

The rachis color, with the vestiture removed, on the adaxial side is dominated by yellow green, olive, and/or olive green hues. The color characteristics of the distal portion of the stipe continue into the rachis. The abaxial side color is dominated by olive, olive green, and/or yellow green hues and merges with the adaxial side color. Specifically, the adaxial side surface color is commonly moderate yellow green (2.5GY5/4) (2.5GY5/6) (5GY5/4), and/or moderate olive green (2.5GY4/4) (5GY4/4), and the abaxial side surface commonly light grayish olive (10Y5/2), grayish olive (10Y4/2), light olive (10Y5/4), moderate olive (10Y4/4), grayish olive green (5GY4/2), moderate olive green (2.5GY4/4) (5GY4/4), and/or moderate yellow green (2.5GY5/4).

The proximal 7–11 pinnae are usually once again pinnate with leaflets petiolulate from the rachilla or sessile to it, and with the distal pinnae on the rachis simple and petiolulate below, becoming sessile above and merging into a single pinnately incised apical blade. The pinnae are predominately alternate with strong opposite tendencies for some basal and apical pinnae and pinnules with compound pinnae being arranged on the rachis with distances between the rachilla insertions on the same side of the rachis usually being between 2 and 10 cm and leaflets on the rachilla on the same side of the rachilla with distances between 1 and 5 cm midway between the rachis and tip and with simple pinnae in the distal part of the frond being arranged on the rachis usually being between 3 and 25 mm, with tendencies to be more closely inserted distally and ultimately merging basally to form the incised trullate apical blade. The plane of the proximal pinna is commonly at an angle of 25°–45° from the plane of the frond with more distal pinnae with tendencies to become increasingly complanate. In the parent plant, the plane of the proximal pinna is commonly at an angle of 50°–80° from the plane of the frond with the inclination of more distal pinnae becoming progressively less.

The blades of the frond are of coriaceous texture with a shiny waxy surface on the adaxial surface and with a glaucous abaxial surface which, on sorus-bearing blades, produce raised sori. The shape of pinnules on compound pinnae is oblong with tendencies to oblong-ovate or elliptical, and with an obtuse base with tendencies to become obliquely asymmetric in the distal portions of the pinna, the margins serrate to dentate, and with an acute to acuminate tip having tendencies to stiffness. The pinnules of the parent plant have tendencies to have a crenate-dentate margin and a broadly acute tip.

The shape of simple leaflet pinnae on the rachis is oblong with tendencies to oblong-ovate or elliptic-oblong with pinnately incised and serrate-dentate margins and with an acute tip having tendencies to stiffness. The simple pinnae of the parent plant have tendencies to be oblong-ovate or oblong-elleptic with pinnately incised and crenate-dentate margins, each segment broadly acute, and with an acute to broadly acute tip.

The apical blade shape, terminating the rachis, is trullate to narrowly so in outline with the tip acuminate but pinnately incised proximal and weakly serrate-dentate on the acuminate proximal lobes. The apical blade of the parent plant differs in having tendencies to be crenate-dentate with the proximal lobes and the tip acute.

The compound pinnae along the proximal portion of the frond are usually between 18 and 28 cm long from the attachment to the rachis to the tip of the distal blade for the proximal compound pinnae, becoming progressively smaller to between 5 and 9 cm for the most distal compound pinna. The width of the pinna across the basal pinnules is Usually between 10 and 22 cm and with the rachilla between 1 and 2 mm in diameter.

The simple pinnae along the distal portion of the rachis is usually between 5 and 9 cm long from rachis to tip for the most proximal pinnae, becoming progressively smaller to usually between 1 and 3 cm for the distal pinnae. The maximum width is usually between 1.5 and 3 cm on the most proximal pinnae, becoming progressively smaller to usually between 0.5 and 1.5 cm for the distal pinnae.

The pinnules on the proximal compound pinnae are usually between 3 and 8 cm long, with a tendency to become smaller distally on the pinna. The width is usually between 1.5 and 3 cm, with tendencies to become smaller distally.

The frond tip has a length usually between 4 and 7 cm when measured from the most distal free pinna and a width usually between 2 and 5 cm. The pinna tips at the proximal portion of the frond have a length usually between 4 and 7 cm when measured from the most distal free pinnule and with a width usually between 1.5 and 4 cm.

Generally, the color of the adaxial surface of the blades is dominated by olive green and yellow green hues, and the abaxial side is dominated by yellow green, olive green, and olive hues exclusive of sori. Specifically, the adaxial color is commonly dark olive green (2.9GY2.3/3.6) (5.6GY2.3/3.6) (7.4GY2.3/4.0), moderate olive green (2.5GY4/4) (5GY4/4) (7.5GY4/4), grayish olive green (5GY3/2), dark yellowish green (8.2GY3.2/6.1), very dark yellowish green (8.9GY2.3/4.7) (0.3G2.2/4.1) (1.4G2.1/4.4), strong yellow green (5GY5/8), and/or moderate yellow green (2.5GY5/6). The abaxial color is commonly moderate yellow green (2.5GY5/4) (2.5GY6/4) (5GY5/4) (5GY6/4) (7.5GY5/4) (7.5GY6/4), moderate olive (10Y4/4), and/or moderate olive green (2.5Y4/4). The adaxial color of the parent plant is commonly dark yellowish green (10GY4/4), strong yellow green (5GY5/8), deep yellow green (6.5GY3.8/7.1) (2.2GY4.3/7.1), and/or moderate olive green (7.5GY4/4) (7.5GY5/6) (5GY4/4) (4.2GY3.3/5.3) (4.5GY3.9/6.9). The abaxial color of the parent plant is commonly moderate yellow green (5GY6/4) (5GY6/6) (5GY7/4) (7.5GY6/4) (7.5GY6/6).

In general, the sori emerge as low flat-topped circular domes on the abaxial surface of the blades, with strong tendencies to lie in a row parallel to the midvein on both sides and to be spaced at intervals usually between 3 and 7 mm along the axis of the blade at a distance between 1 and 3 mm from the nearest strong vein. With maturity, the indusium separates from the epidermis, exposing the sporangia. The indusium is peltate, with an orbicular membrane that shrivels with age. The sporangium is nearly spherical and stalked, and the spores are generally oval.

A mature sorus with exposed sporangia has a diameter usually between 1.0 and 1.7 mm, and with the spheroid portion of the sporangium usually between 0.17 and 0.25 mm. Spores are usually between 0.02 and 0.04 in length and between 0.015 and 0.02 in width.

The color of the sori is commonly dark yellow (5Y6/6), grayish greenish yellow (7.5Y7/4), light olive (7.5Y6/4) (7.5Y5/4)(10Y5/4) (10Y6/4), dark greenish yellow (10Y6/6), and/or moderate yellow green (2.5GY6/6) until the time of the separation of the indusium, and upon the maturation of the sporangia commonly strong brown (5YR4/6)(5YR4/8)(7.5YR4/6), moderate brown (7.5YR4/4), and/or moderate reddish brown (10YR4/4) when observed without the use of magnification.

In the foregoing description, certain terms have been used for brevity, clarity, and understanding, but no unnecessary limitations are to be implied therefrom beyond the requirements of the prior art, because such words are used for description purposes herein and are intended to be broadly construed.

Having now described the invention and the advantageous new and useful characteristics thereof, the new and useful characteristics of the variety of leatherleaf fern are set forth in the appended claims.

What is claimed is:

1. A variety of leatherleaf fern plant distinct from other plants within the species *Rumohra adiantiformis*, the variety having fronds having relatively complanate pinnae, thereby providing fronds having a denser appearance and further providing fronds less susceptible to breakage during harvesting, packing, shipping, and unpacking than fronds of the parent plant.

2. Leatherleaf fern fronds produced by the leatherleaf fern plant in accordance with claim 1.

3. The leatherleaf fern plant variety recited in claim 1, the fronds of which further have the characteristic of more closely subopposite pinnae than those of other plants within the species *Rhumohra adiantiformis*, the fronds thereby presenting a denser appearance than those of the parent plant.

4. Leatherleaf fern fronds produced by the plant in accordance with claim 3.

5. The leatherleaf fern plant recited in claim 3, the fronds of which have a generally darker green color than those of the parent plant.

6. Leatherleaf fern fronds produced by the leatherleaf fern plant in accordance with claim 5.

7. The leatherleaf fern plant recited in claim 5, the fronds of which have a fuller distal acumination than those of the parent plant.

8. Leatherleaf fern fronds produced by the leatherleaf fern plant in accordance with claim 7.

9. A variety of *Rumohra adiantiformis* distinct from other plants within the species *Rumohra adiantiformis* having pinnae meeting a rachis at an angle in a range distinct from and nonoverlapping with a pinnae-rachis angle range of said other plants within the species *Rumohra adiantiformis*, thereby having fronds having a denser appearance and being less susceptible to breakage during positioning a first frond atop a second frond.

10. The variety of *Rumohra adiantiformis* recited in claim 9, wherein the pinnaerachis angle comprises an angle less than 50 degrees.

11. The variety of *Rumohra adiantiformis* recited in claim 9, wherein the pinnaerachis angle comprises an angle in a range of 25–45 degrees.

12. The variety of *Rumohra adiantiformis* recited in claim 9, having fronds having a color in a range of strong olive green to deep olive green.

13. The variety of *Rumohra adiantiformis* recited in claim 9, wherein the fronds have opposite-to-subopposite arrangement of compound pinnae on a rachis, thereby providing a symmetrical appearance to the frond.

14. A variety of leatherleaf fern plant, 'Newbold's Diamond,' deposit number ATCC 97571.

15. A cut frond produced by the leatherleaf fern plant 'Newbold's Diamond,' deposit number ATCC 97571.

16. A rhizome produced by the leatherleaf fern plant 'Newbold's Diamond,' deposit number ATCC 97571.

* * * * *